US008920379B2

(12) United States Patent
Lee

(10) Patent No.: US 8,920,379 B2
(45) Date of Patent: Dec. 30, 2014

(54) NEEDLE UNIT AND DERMATOLOGICAL LIQUID INJECTION APPARATUS USING THE SAME

(75) Inventor: Jong-dae Lee, Seoul (KR)

(73) Assignee: Bomtech Electronics Co., Ltd., Seoul (KR)

( * ) Notice: Subject to any disclaimer, the term of this patent is extended or adjusted under 35 U.S.C. 154(b) by 501 days.

(21) Appl. No.: 13/264,151

(22) PCT Filed: Apr. 14, 2010

(86) PCT No.: PCT/KR2010/002305
§ 371 (c)(1),
(2), (4) Date: Oct. 12, 2011

(87) PCT Pub. No.: WO2010/120111
PCT Pub. Date: Oct. 21, 2010

(65) Prior Publication Data
US 2012/0041374 A1 Feb. 16, 2012

(30) Foreign Application Priority Data
Apr. 14, 2009 (KR) .................. 10-2009-0032316

(51) Int. Cl.
*A61M 5/00* (2006.01)
*A61M 37/00* (2006.01)
*A61M 5/46* (2006.01)

(52) U.S. Cl.
CPC ....... *A61M 37/0076* (2013.01); *A61M 37/0084* (2013.01); *A61M 5/46* (2013.01)
USPC .......................................... 604/173; 606/186

(58) Field of Classification Search
CPC ..................... A61M 37/0076; A61M 37/0084; A61M 37/0092; A61B 17/205
USPC ................................... 606/186, 185; 604/173
See application file for complete search history.

(56) References Cited

U.S. PATENT DOCUMENTS

| 2003/0195542 | A1* | 10/2003 | Lee .............................. 606/186 |
| 2008/0009801 | A1 | 1/2008 | Nickel |
| 2008/0009802 | A1* | 1/2008 | Lambino et al. .............. 604/173 |

FOREIGN PATENT DOCUMENTS

| EP | 1145703 A1 | 10/2001 |
| JP | 2005503194 A | 2/2005 |
| JP | 2007289482 A | 11/2007 |
| KR | 1020060131944 A | 12/2006 |

* cited by examiner

*Primary Examiner* — Kevin C Sirmons
*Assistant Examiner* — Deanna K Hall
(74) *Attorney, Agent, or Firm* — Blank Rome LLP

(57) ABSTRACT

The present invention relates to a needle unit for injecting liquids such as medicine or tattooing pigment spread to a skin, into the skin, and a dermatological liquid injection apparatus using the same. The present invention includes a body unit including a driving device, a cam member rotated by the driving device, and a connecting member reciprocally driven by the cam member; a needle unit detachably mounted to a front end of the body unit; and a rubber member installed to the needle unit, for blocking blood and liquid mixture which are discharged from a skin of a patient and flow into the needle unit, from flowing to the body unit during a medical procedure.

16 Claims, 7 Drawing Sheets

NEEDLE UNIT AND DERMATOLOGICAL LIQUID INJECTION APPARATUS USING THE SAME

TECHNICAL FIELD

Figure 1:
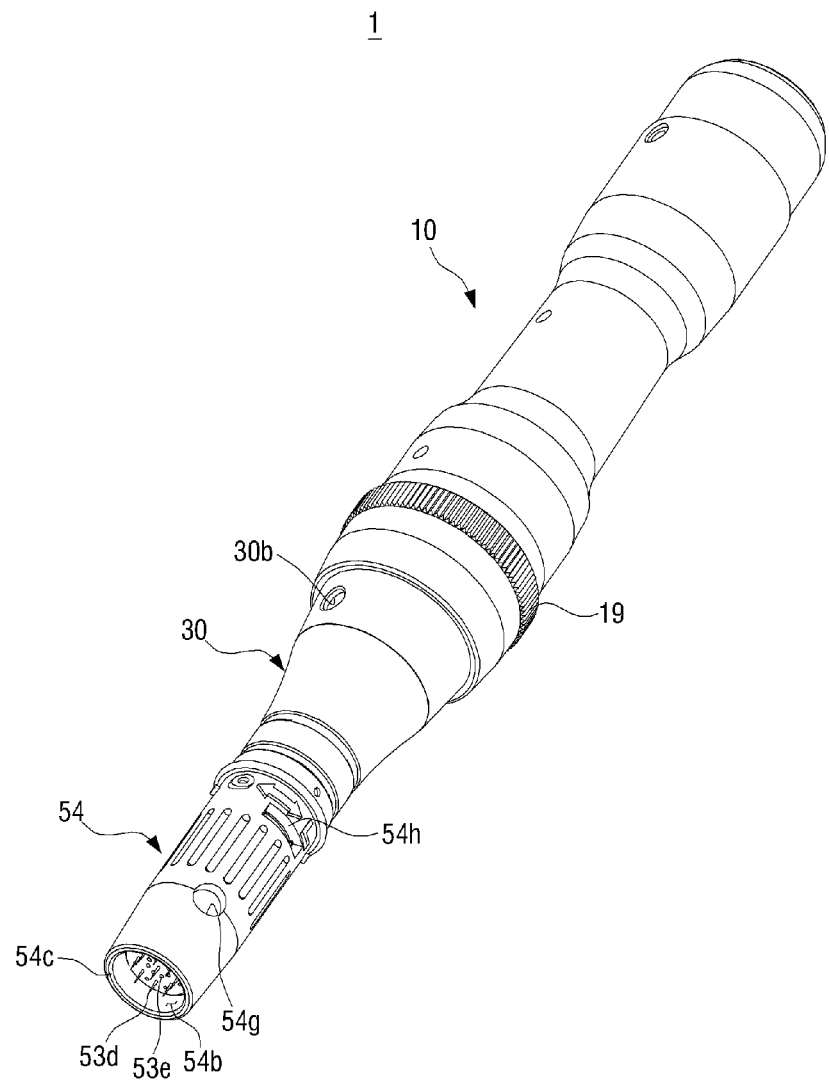

The present invention relates to a needle unit and a dermatological liquid injection apparatus using the same. More particularly, the present invention relates to a needle unit for injecting liquids such as medicine or tattooing pigment spread to a skin, into the skin, and a dermatological liquid injection apparatus using the same.

BACKGROUND ART

Typically, dermatological liquid injection apparatuses indicate apparatuses for injecting a tattooing pigment of a needle unit into the skin or for injecting liquid or gel medicine applied to an affected area of the skin, into the skin.

Such a liquid injection apparatus fabricates a needle unit including a disposable needle for bacterial infections, and mounts the needle unit to a front end of the liquid injection apparatus to use it.

However, although a conventional liquid injection apparatus uses the disposable needle unit, blood and liquid mixture oozing out of the skin frequently flows into a body of the liquid injection apparatus along the disposable needle unit because of the needle during a medical procedure. Since the connection between the needle unit and the main body has a mere mechanical connection structure and cannot block the small amount of the blood flowing into the body, the blood and the liquid mixture of the previously operated person remains in the main body after the liquid injection apparatus is used. Accordingly, it is hard for the conventional liquid injection apparatus to thoroughly block the bacterial infection even when the disposable needle unit is used.

In addition, in the conventional liquid injection apparatus, the needle is guided by a through hole of a cap unit coupled to the main body front end to reciprocate. At this time, the medicine or the tattooing pigment is discharged in the small amount between a needle outer circumference and the through hole. However, when the part between the needle outer circumference and the through hole is clogged in the medical procedure, the supply of the medicine or the pigment is stopped. In this case, it is necessary to replay with a new needle unit.

DETAILED DESCRIPTION OF THE INVENTION

Technical Object of the Invention

Accordingly, an aspect of the present invention is to block blood and liquid mixture of a patient from remaining in a liquid injection apparatus in advance when a disposable needle unit is used.

Another aspect of the present invention is to provide a liquid injection apparatus for smoothly supplying a liquid injected into a needle unit to the skin.

Construction and Operation of the Invention

To achieve the aspects, a liquid injection apparatus includes a body unit including a driving device, a cam member rotated by the driving device, and a connecting member reciprocally driven by the cam member; a needle unit detachably mounted to a front end of the body unit; and a rubber member installed to the needle unit, for blocking blood and liquid mixture which are discharged from a skin of a patient and flow into the needle unit, from flowing to the body unit during a medical procedure.

The needle unit may include a needle support including a plurality of needles and a plurality of liquid discharge holes for ejecting liquid; a liquid reservoir coupled with the needle support in one opening and containing liquid; a movable rod connected to the liquid reservoir with one side and detachably connected to the connecting member with the other end; and a cap unit for surrounding the needle support and the liquid reservoir and including a support unit which the movable rod penetrates, and the rubber member may be disposed between the movable rod, tightly coupled to the support unit of the cap unit with one side, and tightly coupled to part of the movable rod with the other side.

The dermatological liquid injection apparatus may further include a rotation member coupled to the body unit to rotate; and a movable member screw-coupled to the rotation member with one side and detachably coupled to one side of the cap unit with the other side, and the movable member may approach or recede the plurality of the needles to or from an edge unit based on the edge unit which is a front end of the cap unit by moving the cap unit forward and backward when the rotation member rotates in one direction and opposite direction, and sets an insertion depth of the plurality of the needles into the skin.

The edge unit of the cap unit may be disposed perpendicularly to an arrangement direction of the plurality of the needles. The edge unit of the cap unit may be rounded to slide on the skin.

The liquid reservoir may include a first liquid injection hole for injecting the liquid, the cap unit may include a second liquid injection hole overlapping with the first liquid injection hole, and the first liquid injection hole may be in a long hole shape according to a movement direction of the cap unit so as to communicate with the second injection hole even after the cap unit moves forward and backward and changes a location.

The needle unit may include a needle support including a needle; a movable rod connected to the needle support with one side and detachably connected to the connecting member with the other side; a cap unit including the needle support inside to move and containing the injected liquid; and a guide tip coupled to a front end of the cap unit for guiding the needle to reciprocally move to outside, and including a discharge hole for discharging the liquid. The rubber member may be disposed between the movable rod, tightly coupled to the support unit of the cap unit with one side, and tightly coupled to part of the movable rod with the other side.

The dermatological liquid injection apparatus may further include a rotation member rotatably coupled to the body unit; and a moveable member screw-coupled to the rotation member with one side and detachably coupled to one side of the cap unit with the other side. The movable member may approach or recede the needle to or from a front end of the discharge hole based on the front end of the discharge hole of the guide tip by moving the cap unit forward and backward when the rotation member rotates in one direction and opposite direction, and sets an insertion depth of the needle into the skin.

When the rotation member rotates in one direction and opposite direction, the movable member may straightly move forward and backward along the support member installed inside the body unit, without rotating.

The support member may form a guide hole in a long hole shape along a longitudinal direction of the support member, the movable member may include a through hole a rotation preventing bolt penetrates, and the rotation preventing bolt may be inserted to the guide hole by passing through the through hole and.

The dermatological liquid injection apparatus may further include a coil spring coupled to the movable rod, supported by the support unit of the cap unit with one end, and supported by part of the movable rod with the other end.

Effect of the Invention

As set forth above, according to the present invention, when the plurality of the needles is inserted to and withdrawn from the skin and the blood and the liquid mixture oozing out of the skin flows into the needle unit, the rubber member basically blocks them from flowing into the body unit and remaining in the body unit. Thus, when the liquid injection apparatus is used, the bacterial injection of the patient from the remaining block can be prevented.

Further, even when the tiny gaps between the plurality of the needles and the needle support are clogged, the liquid can be smoothly discharged to the skin through the plurality of the liquid discharge holes.

THE BRIEF DESCRIPTION OF THE DRAWINGS

Figure 2:
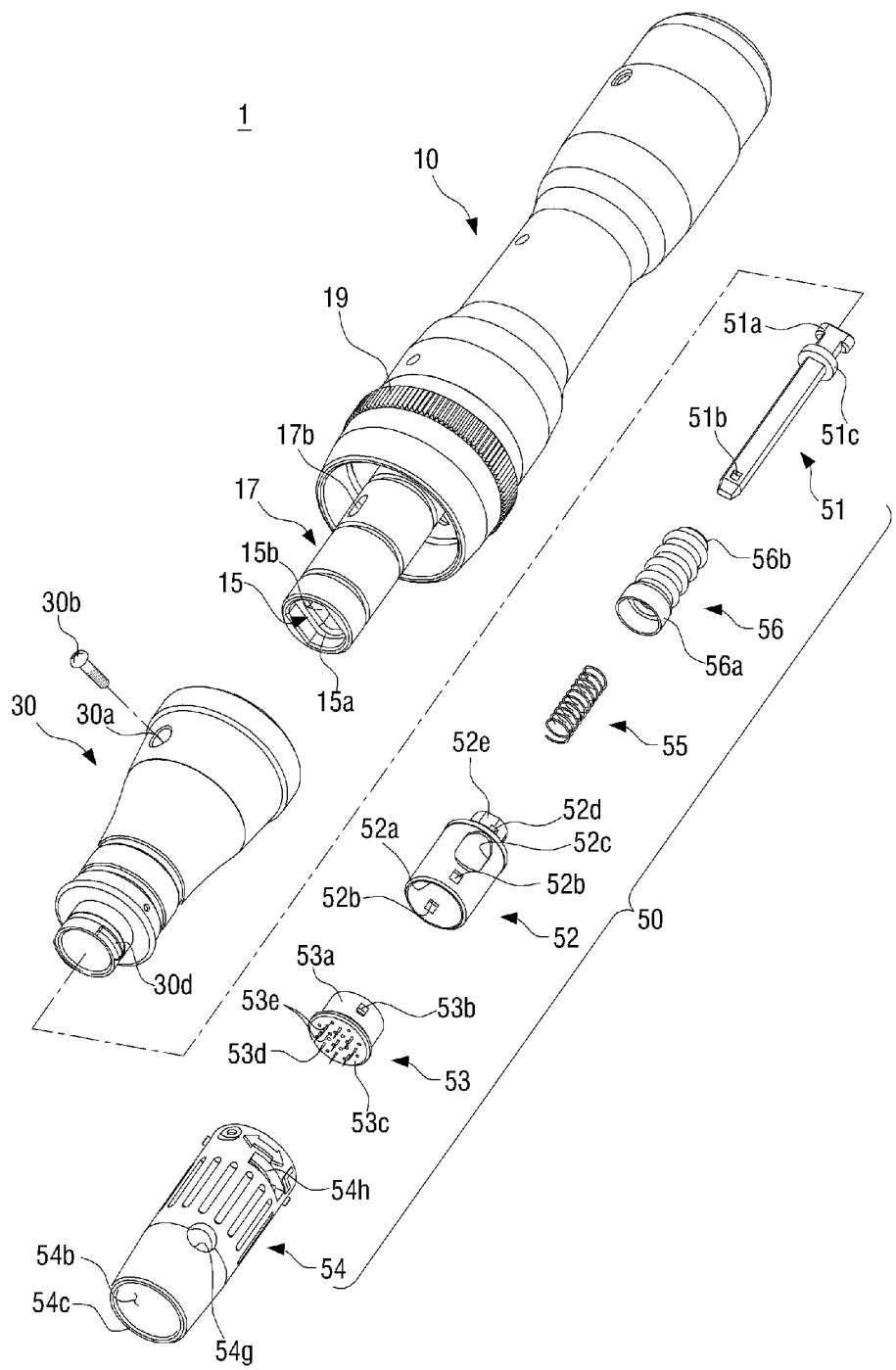
Figure 3:
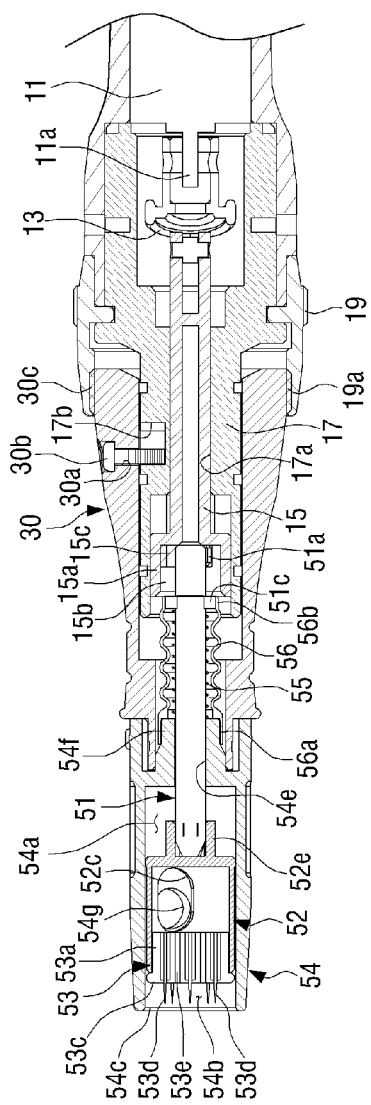
Figure 4:
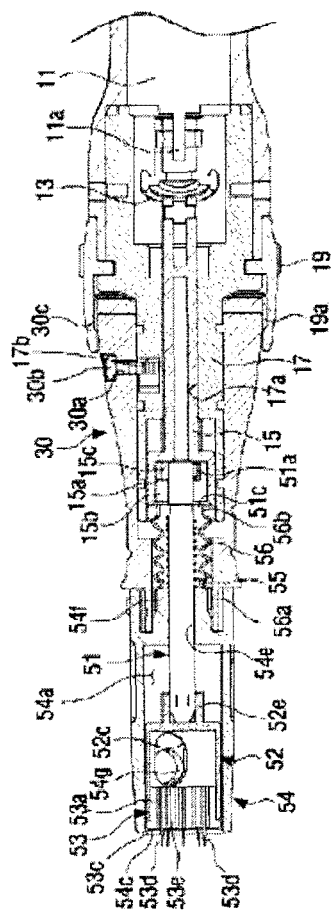
Figure 5:
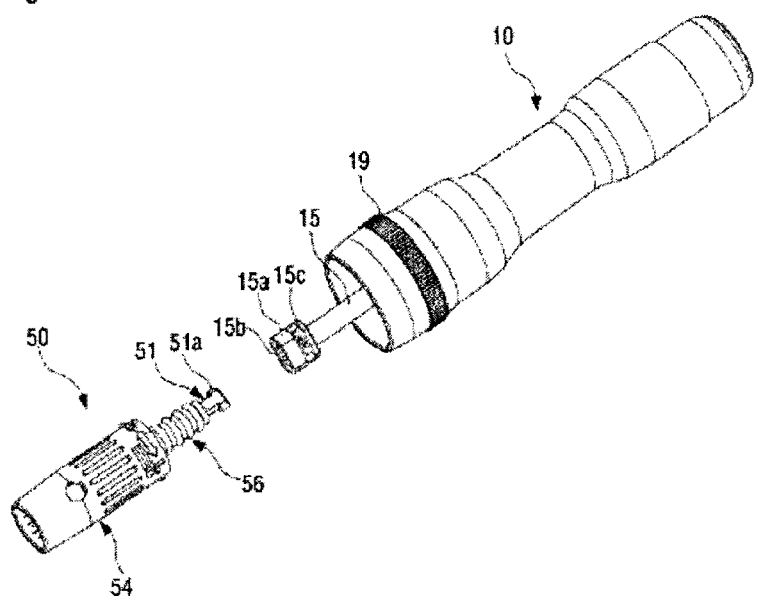
Figure 6:
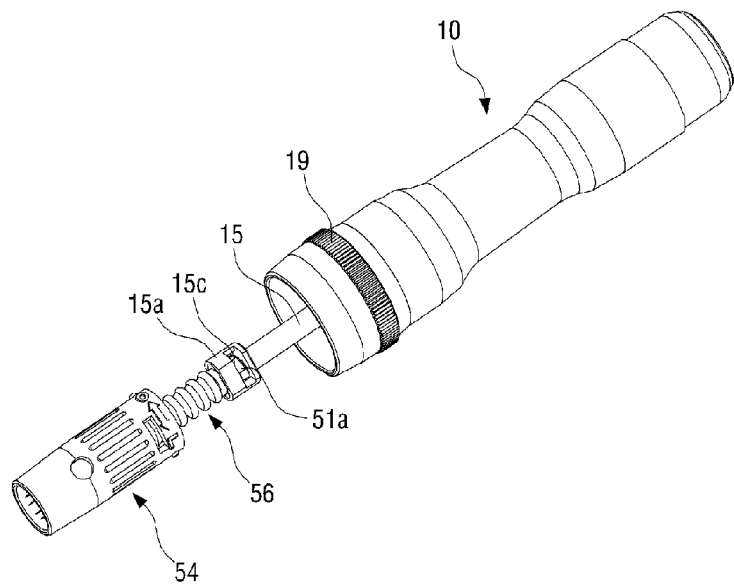
Figure 7:
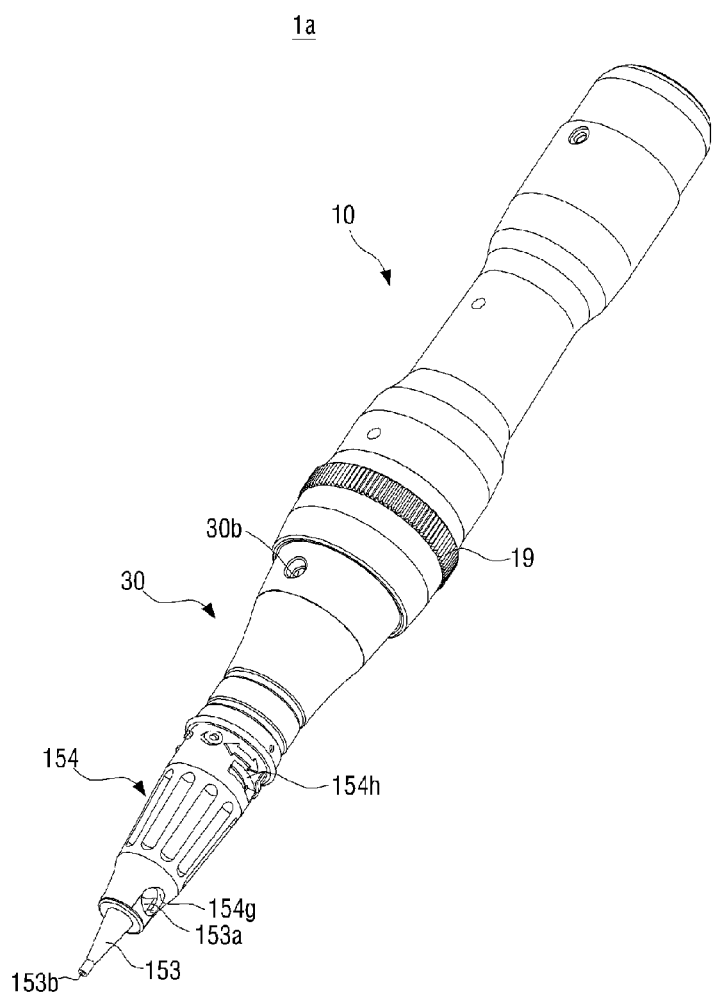
Figure 8:
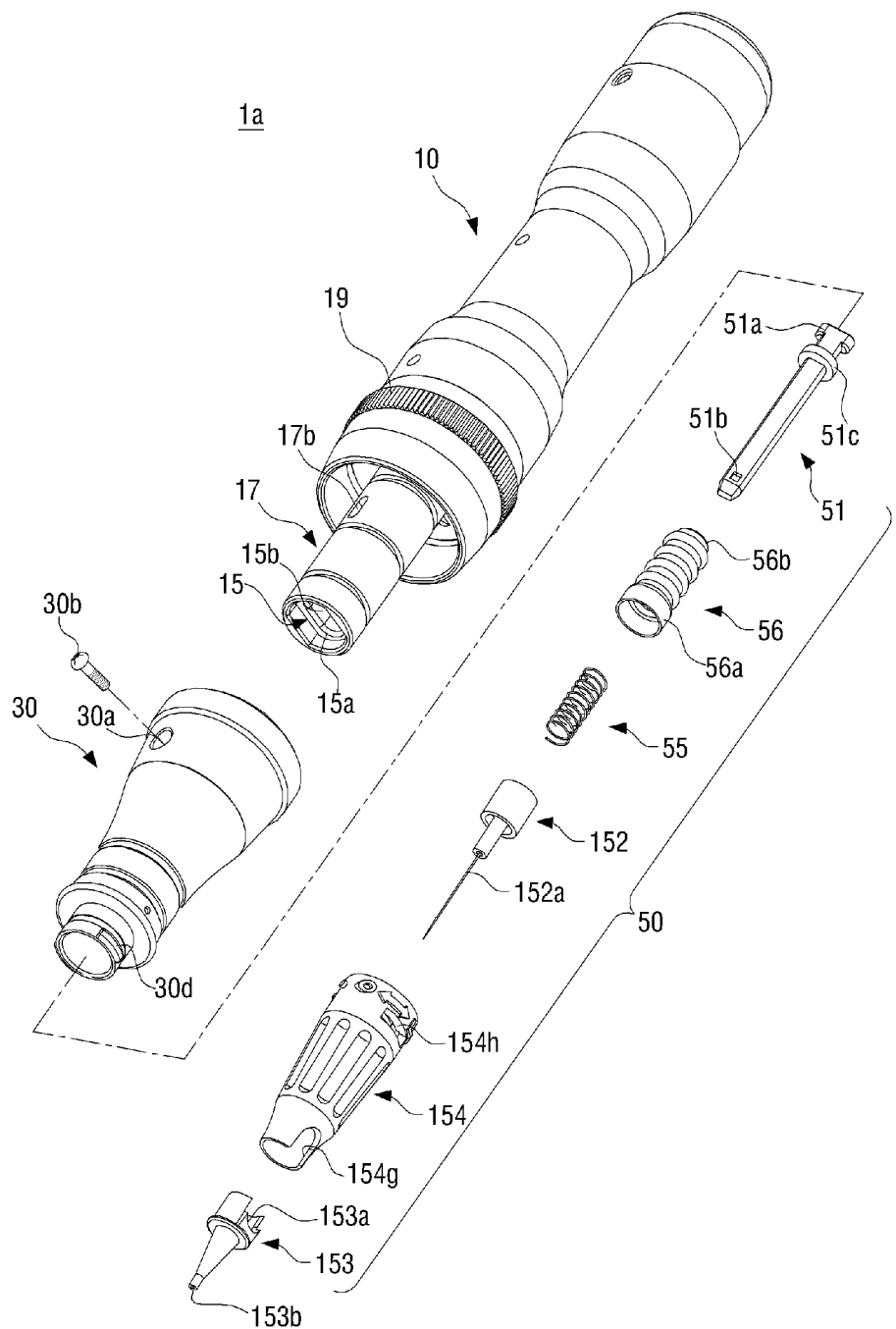
Figure 9:
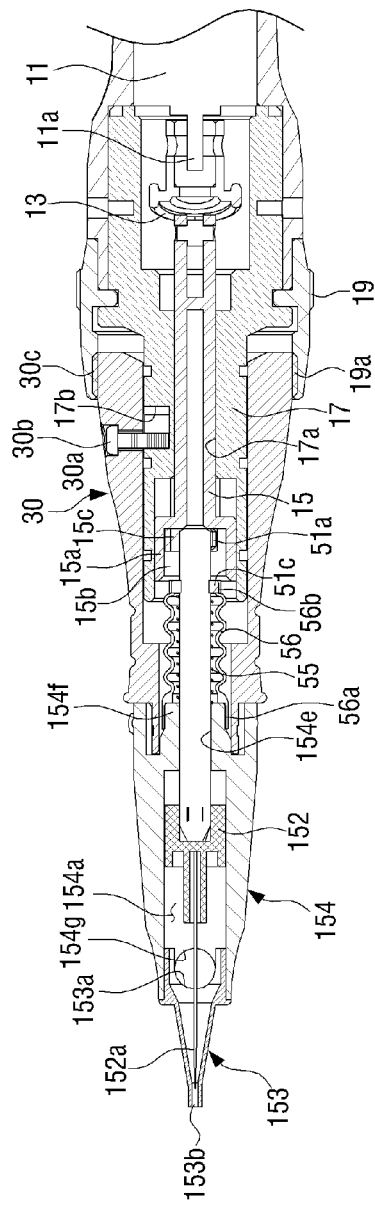

FIG. 1 is an assembly perspective view of a dermatological liquid injection apparatus according to one embodiment of the present invention, FIG. 2 is an exploded perspective view of the dermatological liquid injection apparatus according to one embodiment of the present invention, FIGS. 3 and 4 are partial cross-sectional views of the dermatological liquid injection apparatus according to one embodiment of the present invention, FIGS. 5 and 6 are simplified perspective views of assembly of a needle unit with a support member and a movable member omitted, FIG. 7 is an assembly perspective view of a dermatological liquid injection apparatus according to another embodiment of the present invention, FIG. 8 is an exploded perspective view of the dermatological liquid injection apparatus according to another embodiment of the present invention, FIG. 9 is a partial cross-sectional view of the dermatological liquid injection apparatus according to another embodiment of the present invention.

BEST MODE FOR CARRYING OUT THE INVENTION

Hereinafter, a structure of a dermatological liquid injection apparatus according to embodiments of the present invention is explained by referring to the attached drawings.

First, a liquid injection apparatus 1 according to one embodiment of the present invention includes a body unit 10, a movable member 30, and a needle unit 50.

Referring to FIG. 1, the body unit 10 is formed in a cylindrical shape with a certain length so that an operator can grab it with a hand. The body unit 10 accommodates a driving motor 11 and various electric components (not shown) for transferring external power to the driving motor 11 as shown in FIG. 3. A driving shaft 11a of the driving motor 11 is coupled with a cam member 13.

Referring to FIG. 3, the cam member 13 is contacted with one end of a connecting member 15 detachably connected to the needle unit 50. In this case, the cam member 13 is rotated by the driving shaft 11a and makes the connecting member 15 reciprocate in a longitudinal direction of the body unit 10.

One side of the connecting member 15 penetrates and is coupled with one side to slide along the inner side of a support member 17 secured to the body unit 10. The connecting member 15 includes an insertion hole 15b formed at a front end 15a exposed to one end of the support member 17, and includes a snap coupling hole 15c formed in one cylindrical surface of the front end 15a.

The support member 17 protrudes to one side in a certain length along the longitudinal direction of the body unit 10, and forms a through hole 17a so that the connecting member 15 slides and reciprocates along the inner side. The support member 17 forms a guide hole 17b along the longitudinal direction of one cylindrical surface. According to the insertion of a rotation preventing bolt 30b to be explained, the guide hole 17b guides the movable member 30 to move in a straight direction over a certain distance without rotating. In addition, a rotation member 19 of a ring shape is rotatably coupled to the outer circumference of the support member 17.

The rotation member 19 includes a screw unit 19a formed in an inner circumference surface of the front end. The screw unit 19a is screw-connected with a screw unit 30c of the movable member 30. Hence, when the rotation member 19 rotates in one direction and opposite direction, the movable member 30 linked to the rotation member 19 moves forward and backward. The rotation member 19 sets the protrusion length of a plurality of needles 53d of the needle unit 50 from a front end edge unit 54c of the cap unit 54 by regulating the movement direction and the movement distance of the movable member 30 as shown in FIGS. 3 and 4, and thus can arbitrarily set the insertion length of the needles 53d into the skin.

Referring to FIGS. 2 and 3, the movable member 30 surrounds the circumference of the support member 17, and a bolt assembly hole 30a screw-coupled with the rotation preventing bolt 30b is formed in one circumference surface. The low part of the rotation preventing bolt 30b passes through the bolt assembly hole 30a and is inserted to the guide hole 17b. Thus, when the rotation member 19 is rotated in one direction and opposite direction, the rotation preventing bolt 30b prevents the movable member 30 connected to the rotation member 19 by the screw units 19a and 30c from rotating together with the rotation member 19 and guides to move in the straight direction at the same time.

The movable member 30 includes a first coupling projection 30d snap-coupled with a first coupling hole 54h formed in a rear end of the cap unit 54. Hence, when the movable member 30 moves forward and backward, the cap unit 54 moves forward and backward together with the movable member 30.

The needle unit 50 includes a movable rod 51, a liquid reservoir 52, a needle support 53, the cap unit 54, a coil spring 55, and a rubber member 56.

The movable rod 51 includes a latching projection 51a detachably coupled to the snap coupling hole 15c of the connecting member 15 with the rear end to receive the driving force from the connecting member 15. Also, the movable rod 51a includes a second coupling projection 51b detachably coupled to a second coupling hole 52d of the liquid reservoir 52 at the front end.

The liquid reservoir 52 is formed roughly in a cylindrical shape, forms an opening 52a communicating with the needle support 53 in one side, and forms a third coupling hole 52b detachably coupled with a third coupling projection 53b of the needle support 53 in the inner circumference surface on the side of the opening 52a. The liquid reservoir 52 also forms a first liquid injection hole 52c of a long hole shape in one side, and forms a connection projection 52e including a second coupling hole 52d at the rear end.

The needle support 53 is formed roughly in a cylindrical shape, a portion 53a of a rear part is detachably inserted to the liquid reservoir 52 through the opening 52a, and the third coupling projection 53b is formed in the outer circumference surface of the portion 53a. Also, the needle support 53 is coupled with the plurality of the needles 53d protruding at intervals in the front side 53c which is a plane surface, and a plurality of liquid discharge holes 53e is formed between the needles 53d.

The cap unit 54 is formed roughly in a cylindrical shape, and includes therein a movable place 54a where the liquid reservoir 52 and the needle support 53 mutually coupled can reciprocate forward and backward. Also, the cap unit 54 forms the edge unit 54c in the front end, and forms an opening 54b for protruding the plurality of the needles 53d outside the edge part 54c. When the liquid injection apparatus 1 is used, the edge unit 54c moves in direct contact with the skin. At this time, the rounding is formed not to scratch the skin. Also, the edge unit 54c is disposed approximately perpendicular to the arrangement direction of the plurality of the needles 53d.

Further, the cap unit 54 forms a support unit 54f in the inner rear side, including a through hole 54e to which the movable rod 51 is inserted. In this case, since the through hole 54e is formed the same as the cross-sectional shape of the movable rod 51 which is approximately rectangular, the sliding movable rod 51 reciprocally moves along the through hole 54e without rotating.

The cap unit 54 forms a second liquid injection hole 54g in one circumference surface, and the second liquid injection hole 54g maintains overlapping with the first liquid injection hole 52c so as to inject the liquid into the liquid reservoir 52 through the first liquid injection hole 52c. In this case, the second liquid injection hole 54g is approximately circular, unlike the first liquid injection hole 52c of the long hole shape. As such, the first liquid injection hole 52c is in the long hole shape according to the movement direction of the cap unit 54. Hence, although a location of the second liquid injection hole 54g is changed when the rotation member 19 rotates and the cap unit 54 moves forward and backward over a certain distance, the second liquid injection hole 54g always keeps overlapping with the first liquid injection hole 52c so that the liquid can be injected to the liquid reservoir 52 through the first and second liquid injection holes 52c and 54g.

The coil spring 55 is coupled to the movable rod 51, supported by a fixing protrusion 51c of the movable rod 51 with one end, and supported by the support unit 54f of the cap unit 54 with the other end. Hence, when the needle unit 50 fabricated as the package as shown in FIG. 5 is coupled to the body unit 10 as shown in FIG. 6, the coil spring 55 elastically supports the movable rod 51 not to be pushed while the coupling projection 51a of the movable rod 51 is inserted to the insertion hole 15b of the connecting member 15, and thus can stably snap-couple the coupling projection 51a of the movable rod 51 to the snap coupling hole 15c of the connecting member 15.

The rubber member 56 is formed roughly in a cylindrical shape having folds like jabara and formed of a rubber material or a synthetic resin material having certain elasticity. The rubber member 56 is disposed between the movable rod 51 and the cap unit 54 to block the blood flowing into the cap unit 54 from moving to the body unit 10 during the medical procedure. That is, the rubber member 56 is tightly coupled to retain the airtight while one side 56a surrounds the support unit 54f of the cap unit 54, and tightly coupled to retain the airtight while the other side surrounds the fixing protrusion 51c of the movable rod 51. Hence, the blood flowing into the cap unit 54, which flows to the back of the movable rod 51 through the through hole 54e of the cap unit 54, merely remains inside the rubber member 56 and cannot move to the body unit 10.

Further, on account of the corrugated shape and the elasticity, the rubber member 56 absorbs vibrations produced by inertial force generating in the connection part of the connecting member 15 and the movable rod 51 which reciprocate when the liquid injection apparatus operates, and inertial force generated by the reciprocating drive of the liquid reservoir 52 and the needle support 53, with respect to the whole rubber member 56, and thus can reduce the vibrations and noise according to the vibrations.

In addition, the rubber member 56 can function as the coil spring 55 using its elasticity at the same time. Thus, the liquid injection apparatus I of one embodiment can be used with the coil spring 55 omitted.

When the needle unit 50 is separated from the body unit 10, the rubber member 56 makes the needle support 53 always stay inside the cap unit 54 so as to prevent the needles 53d from exposing outside the cap unit 54. As such, since the needles 53d, which are separated from the body unit 10, lie inside the cap unit 54, it prevents the operator or the patient from being pricked by the needles 54d. In addition, after the needle unit 50 is used, the infection from the blood or the liquid mixture stained on the needles 53d can be blocked in advance.

The operation of the liquid injection apparatus constructed according to one embodiment of the present invention is described by referring to FIGS. 3 through 6.

First, the movable rod 51 of the disposable needle unit 50 which is fabricated as the package as shown in FIG. 5 is snap-coupled to the connecting member 15 of the body unit 10 as shown in FIG. 6.

Next, certain liquid is injected into the liquid reservoir 52 through the first and second liquid injection holes 52c and 54g. This liquid corresponds to the tattoo pigment for the tattooing or a certain medicine for the treatment.

As such, when the liquid injection to the liquid reservoir 52 is finished, the operator grips the body unit 10 and applies the power to the driving motor 11 while the edge unit 54c of the cap unit 54 is closely contacted with the skin of the patient.

The cam member 13 is rotated by the driving motor 11 and thus the connecting member 15 reciprocally drives in the straight direction along the longitudinal direction of the liquid injection apparatus 1. The movable rod 51 coupled to the connecting member 15 reciprocally drives in a straight direction to reciprocally move the liquid reservoir 52 and the needle support 53 forward and backward at a high speed within the movable space 54a of the cap unit 54.

At this time, as the pressure inside the liquid reservoir 52 rises, the liquid contained in the liquid reservoir 52 is ejected through the plurality of the liquid discharge holes 53e. The liquid is also ejected through tiny gaps (not shown) between the plurality of the needles 53d and the needle support 53 which the needles 53 pass through.

When the plurality of the needles 53d is repeatedly inserted to the skin, the ejected liquid permeates into the skin together with the needles 53d and thus the penetration action is carried out.

In this case, the liquid injection apparatus 1 of the present invention can smoothly discharge the liquid to the skin through the plurality of the liquid discharge holes 53e even when the tiny gaps (not shown) between the needles 53d and the needle support 53 are clogged.

Further, when the plurality of the needles 53d is inserted to and withdrawn from the skin and the blood oozing out of the skin flows into the needle unit 50, the rubber member 56 thoroughly blocks the blood from flowing into and remaining in the body unit 10 and thus the bacterial infection can be prevented basically.

Hereafter, the dermatological liquid injection apparatus according to another embodiment of the present invention is explained by referring to FIGS. 7 through 9.

The liquid injection apparatus 1a according to another embodiment of the present invention has the same structure, except for a needle unit 150, as the liquid injection apparatus 1 of the one embodiment as stated above. Accordingly, in the liquid injection apparatus 1a according to another embodiment to be explained, the overlapping components with the one embodiment are omitted.

The needle unit 150 in another embodiment includes the movable rode 51, a needle support 152, a guide tip 153, a cap unit 154, the coil spring 55, and the rubber member 56. Among them, the movable rod 51, the coil spring 55, and the rubber member 56 have the same structures as in one embodiment and thus shall be omitted.

The needle support 152 has an external diameter corresponding to the inner circumference of a movable space 154a of the cap unit 154, and a single needle 152a is securely installed in the center. In this case, as the needle support 152 is detachably connected to the movable rod 51, it is linked to the movable rod 51.

The guide tip 153 is detachably coupled to the front end of the cap unit 154 with the rear side, and a first liquid injection groove 153a is formed in part of the rear side. In the front side of the guide tip 153, a discharge hole 153b is formed where the needle 152a reciprocally penetrates and the liquid injected to the movable space 154a of the cap unit 154 is discharged at the same time.

The cap unit 154 is formed roughly in a cylindrical shape, and includes therein the movable space 154 where the needle support 152 can reciprocate forward and backward. The movable space 154a is also used as the space for containing the liquid. Also, a support unit 154f having a through hole 154e to which the movable rod 51 is inserted is formed in the inner back side of the cap unit 154. In this case, since the through hole 154e is formed the same as the cross section of the movable rod 51 formed roughly in the rectangular shape, it prevents the movable rod 51 from rotating when the movable rod 51 slides along the through hole 154e. Also, the cap unit 154 includes a first liquid injection groove 153a in part of the front end and a second liquid injection groove 154g forming a liquid injection hole.

Meanwhile, similarly to the one embodiment, since the rubber member 56 can simultaneously function as the coil spring 55 through its elasticity in another embodiment, the liquid injection apparatus in of another embodiment can be also used without the coil spring 55.

The liquid injection apparatus 1a according to another embodiment can basically block the blood oozing out of the skin from flowing into the needle unit 50 using the rubber member 56 and from flowing to and remaining in the body unit 10 as in one embodiment. Further, similarly to the one embodiment, since the cap unit 154 is moved forward and backward when the rotation member 19 rotates in one direction and opposite direction in another embodiment, the needle 152a approaches or recedes to or from the front end of the discharge hole I 53b based on the front end of the discharge hole 153b of the guide tip 153 and thus the skin insertion depth of the needle 152a can be set.

What is claimed is:
1. A liquid injection apparatus comprising:
a body unit comprising a driving device, a cam member rotated by the driving device, and a connecting member reciprocally driven by the cam member;
a needle unit detachably mounted to a front end of the body unit; and
a rubber member installed to the needle unit, for blocking blood and liquid mixture which are discharged from a skin of a patient and flow into the needle unit, from flowing to the body unit during a medical procedure,
wherein the needle unit comprises:
a needle support comprising a plurality of needles and a plurality of liquid discharge holes for ejecting liquid;
a liquid reservoir coupled with the needle support in one opening and containing liquid;
a movable rod connected to the liquid reservoir with one side and detachably connected to the connecting member with the other end; and
a cap unit for surrounding the needle support and the liquid reservoir and comprising a support unit which the movable rod penetrates,
wherein the liquid reservoir forms a first liquid injection hole of a long hole shape in one side, and the cap unit forms a second liquid injection hole in one circumference surface.
2. The dermatological liquid injection apparatus of claim 1, wherein the rubber member is disposed between the movable rod, tightly coupled to the support unit of the cap unit with one side, and tightly coupled to part of the movable rod with the other side.
3. The dermatological liquid injection apparatus of claim 2, further comprising:
a rotation member coupled to the body unit to rotate; and
a movable member screw-coupled to the rotation member with one side and detachably coupled to one side of the cap unit with the other side,
wherein the movable member approaches or recedes the plurality of the needles to or from an edge unit based on the edge unit which is a front end of the cap unit by moving the cap unit forward and backward when the rotation member rotates in one direction and opposite direction, and sets an insertion depth of the plurality of the needles into the skin.
4. The dermatological liquid injection apparatus of claim 2, wherein the edge unit of the cap unit is disposed perpendicularly to an arrangement direction of the plurality of the needles.
5. The dermatological liquid injection apparatus of claim 2, wherein the edge unit of the cap unit is rounded to slide on the skin.
6. The dermatological liquid injection apparatus of claim 2, wherein the liquid reservoir comprises a first liquid injection hole for injecting the liquid, the cap unit comprises a second liquid injection hole overlapping with the first liquid injection hole, and
the first liquid injection hole is in a long hole shape according to a movement direction of the cap unit so as to communicate with the second injection hole even after the cap unit moves forward and backward and changes a location.
7. A liquid injection apparatus comprising:
a body unit comprising a driving device, a cam member rotated by the driving device, and a connecting member reciprocally driven by the cam member;
a needle unit detachably mounted to a front end of the body unit; and a rubber member installed to the needle unit, for blocking blood and liquid mixture which are discharged from a skin of a patient and flow into the needle unit, from flowing to the body unit during a medical procedure, wherein the needle unit comprises:
- a needle support comprising a needle;
- a movable rod connected to the needle support with one side and detachably connected to the connecting member with the other side;
- a cap unit comprising the needle support inside to move and containing the injected liquid; and
- a guide tip coupled to a front end of the cap unit for guiding the needle to reciprocally move to outside, and comprising a discharge hole for discharging the liquid,
- wherein the rubber member is disposed between the movable rod, tightly coupled to the support unit of the cap unit with one side, and tightly coupled to part of the movable rod with the other side,
- wherein the guide tip includes a first liquid injection groove formed in part of the rear side, and the cap unit includes a second liquid injection groove.

8. The dermatological liquid injection apparatus of claim 7, further comprising:
- a rotation member rotatably coupled to the body unit; and
- a moveable member screw-coupled to the rotation member with one side and detachably coupled to one side of the cap unit with the other side,
- wherein the movable member approaches or recedes the needle to or from a front end of the discharge hole based on the front end of the discharge hole of the guide tip by moving the cap unit forward and backward when the rotation member rotates in one direction and opposite direction, and sets an insertion depth of the needle into the skin.

9. The dermatological liquid injection apparatus of claim 8, wherein, when the rotation member rotates in one direction and opposite direction, the movable member straightly moves forward and backward along the support member installed inside the body unit, without rotating.

10. The dermatological liquid injection apparatus of claim 9, wherein the support member forms a guide hole in a long hole shape along a longitudinal direction of the support member, and the movable member comprises a through hole a rotation preventing bolt penetrates,
- wherein the rotation preventing bolt is inserted to the guide hole by passing through the through hole and.

11. The dermatological liquid injection apparatus of claim 2 or claim 7, further comprising:
- a coil spring coupled to the movable rod, supported by the support unit of the cap unit with one end, and supported by part of the movable rod with the other end.

12. A needle unit of a dermatological liquid injection apparatus for injecting liquid such as medicine or tattooing pigment spread onto a skin, into the skin, comprising:
- a needle support comprising a plurality of needles and a plurality of liquid discharge holes for ejecting liquid;
- a liquid reservoir coupled with the needle support in one opening and containing liquid;
- a movable rod connected to the liquid reservoir with one side and detachably connected to one end of a driving unit in the liquid injection apparatus with the other side; and
- a cap unit for surrounding the needle support and the liquid reservoir and comprising a support unit the movable rod penetrates,
- wherein the liquid reservoir forms a first liquid injection hole of a long hole shape on one side, and the cap unit forms a second liquid injection hole in one circumference surface.

13. The needle unit of claim 12, wherein an edge unit of the cap unit is disposed perpendicularly to an arrangement direction of the plurality of the needles.

14. The needle unit of claim 12, wherein the edge unit of the cap unit is rounded to slide on the skin.

15. A needle unit of a dermatological liquid injection apparatus for injecting liquid such as medicine or tattooing pigment spread onto a skin, into the skin, comprising:
- a needle support comprising a needle;
- a movable rod connected to the needle support with one side and detachably connected to one end of a driving unit in the liquid injection apparatus with the other side;
- a cap unit accommodating the needle support to move and containing the injected liquid; and
- a guide tip coupled to a front end of the cap unit for guiding the needle to reciprocally move to outside, and comprising a discharge hole for discharging the liquid,
- wherein the guide tip includes a first liquid injection groove formed in part of the rear side, and the cap unit includes a second liquid injection groove.

16. The needle unit of claim 12 or claim 15, further comprising:
- a coil spring coupled to the movable rod, supported by the support unit of the cap unit with one end, and supported by part of the movable rod with the other end.

* * * * *